(12) United States Patent
Zollinger et al.

(10) Patent No.: US 9,211,387 B2
(45) Date of Patent: *Dec. 15, 2015

(54) INFANT NASAL INTERFACE MASK

(75) Inventors: Chris Zollinger, Chino Hills, CA (US); Brian Pierro, Yorba Linda, CA (US)

(73) Assignee: CareFusion 2200, Inc., San Diego, CA (US)

( * ) Notice: Subject to any disclaimer, the term of this patent is extended or adjusted under 35 U.S.C. 154(b) by 823 days.

This patent is subject to a terminal disclaimer.

(21) Appl. No.: 12/819,549

(22) Filed: Jun. 21, 2010

(65) Prior Publication Data

US 2010/0258128 A1  Oct. 14, 2010

Related U.S. Application Data

(63) Continuation of application No. 11/292,784, filed on Dec. 2, 2005, now Pat. No. 7,762,258.

(51) Int. Cl.
*A62B 18/08* (2006.01)
*A61M 16/06* (2006.01)

(52) U.S. Cl.
CPC ............ *A61M 16/06* (2013.01); *A61M 16/0616* (2014.02); *A61M 16/0666* (2013.01)

(58) Field of Classification Search
CPC ............ A61M 16/06; A61M 16/0616; A61M 16/0666
USPC ............. 128/205.25, 206.11, 206.12, 206.15, 128/206.21, 206.24, 206.26, 206.27, 128/206.28, 207.12, 207.13, 207.18
See application file for complete search history.

(56) References Cited

U.S. PATENT DOCUMENTS

| | | | |
|---|---|---|---|
| 2,749,910 A | | 6/1956 | Faulconer, Jr. |
| 3,216,413 A | * | 11/1965 | Arecheta Mota ........ 128/205.13 |
| 4,655,213 A | | 4/1987 | Rapoport et al. |
| 4,907,584 A | | 3/1990 | McGinnis |

(Continued)

FOREIGN PATENT DOCUMENTS

| DE | 19603949 A1 | 8/1997 |
|---|---|---|
| JP | 11000397 A | 1/1999 |

(Continued)

OTHER PUBLICATIONS

Entire Specification of U.S. Appl. No. 60/632,121, filed Jan. 12, 2005 of U.S. Pub 2009/0000623 to Lynch.*

(Continued)

*Primary Examiner* — Victoria J Hicks
(74) *Attorney, Agent, or Firm* — McDermott Will & Emery LLP

(57) ABSTRACT

An infant nasal interface mask for use with a nasal continuous positive airway pressure (nCPAP) system including a mask body and a base. The mask body forms a cavity and is defined by a leading portion, an intermediate shell portion, and a trailing portion. The leading portion terminates in a leading edge forming an aperture open to the cavity and having a generally triangular shape for placement over a patient's nose. The trailing portion includes a bellows segment characterized by an increased flexibility as compared to a flexibility of the intermediate shell portion. The base extends from the trailing portion opposite the leading portion and forms at least one longitudinal passage extending through a thickness of the base and fluidly connected to the cavity. The intermediate shell portion is laterally pivotable relative to the base via the bellows segment.

22 Claims, 6 Drawing Sheets

(56) References Cited

U.S. PATENT DOCUMENTS

| | | |
|---|---|---|
| 4,944,310 A | 7/1990 | Sullivan |
| 5,243,971 A | 9/1993 | Sullivan et al. |
| 5,429,683 A | 7/1995 | Le Mitouard |
| 5,560,354 A | 10/1996 | Berthon-Jones et al. |
| 5,687,715 A | 11/1997 | Landis et al. |
| 5,921,239 A | 7/1999 | McCall et al. |
| 6,427,694 B1 * | 8/2002 | Hecker et al. ............ 128/206.21 |
| 6,729,333 B2 | 5/2004 | Barnett et al. |
| 6,772,760 B2 * | 8/2004 | Frater et al. ............. 128/206.24 |
| 7,762,258 B2 * | 7/2010 | Zollinger et al. ........ 128/206.24 |
| 7,900,630 B2 * | 3/2011 | Geiselhart et al. ....... 128/206.24 |
| 2003/0200970 A1 * | 10/2003 | Stenzler et al. .......... 128/207.18 |
| 2004/0244804 A1 | 12/2004 | Olsen et al. |
| 2005/0051177 A1 | 3/2005 | Wood et al. |
| 2005/0092329 A1 * | 5/2005 | Sta-Maria ................ 128/207.18 |
| 2006/0283456 A1 | 12/2006 | Geiselhart et al. |
| 2009/0000623 A1 * | 1/2009 | Lynch et al. ............. 128/206.24 |

FOREIGN PATENT DOCUMENTS

| | | |
|---|---|---|
| JP | 2004321549 A | 11/2004 |
| RU | 2004100276 A | 2/2005 |
| WO | 03000310 A2 | 1/2003 |
| WO | 2004096332 A1 | 11/2004 |

OTHER PUBLICATIONS

PCT Search Report mailed Jan. 17, 2008 (10 pages).
Official Action from the Patent Office of the Russian Federation mailed Sep. 28, 2010 (6 pages).
Chinese Office Action issued Sep. 27, 2010 (15 pgs.).

* cited by examiner

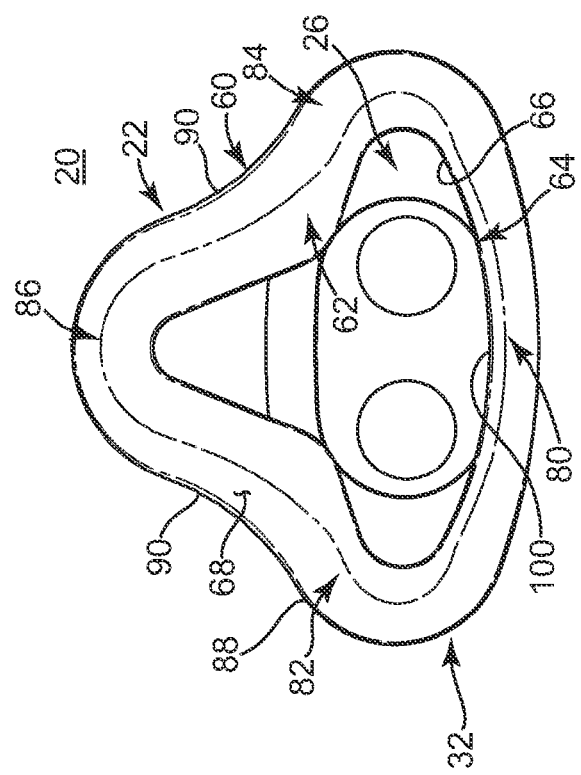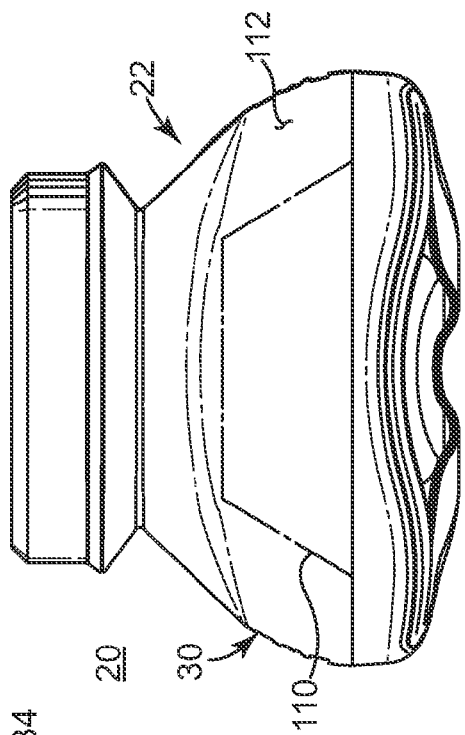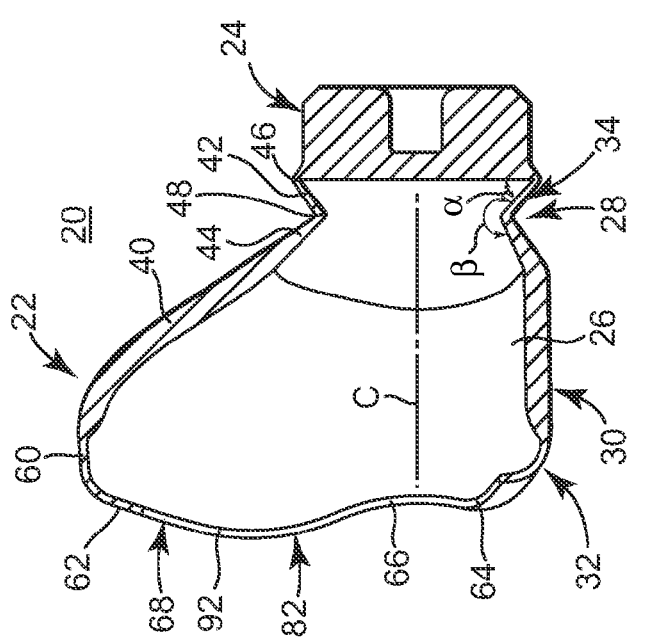

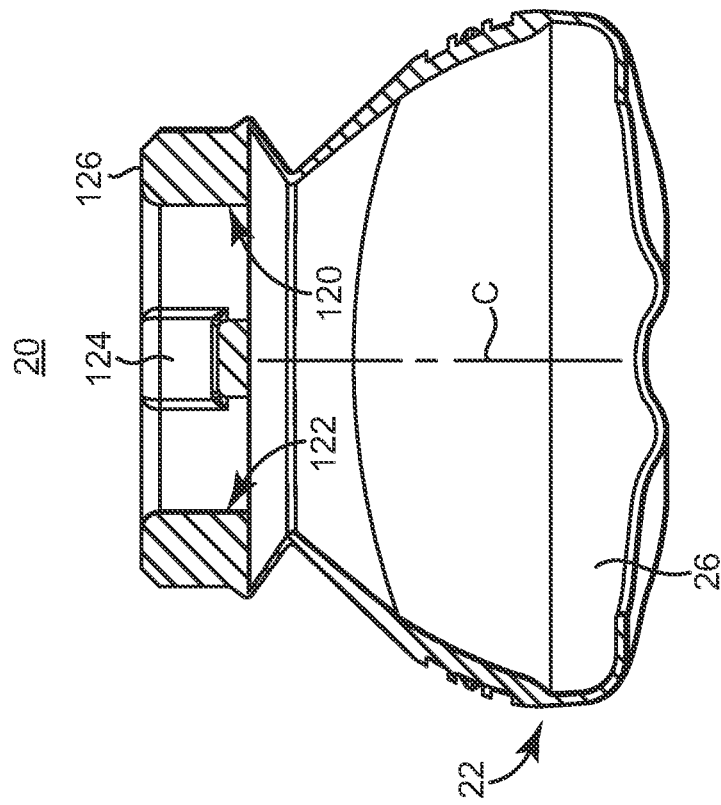
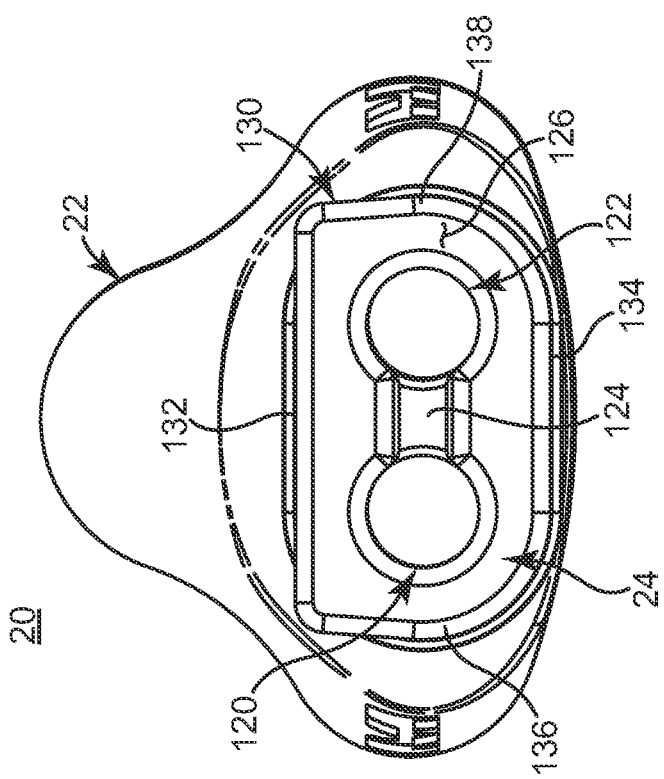

INFANT NASAL INTERFACE MASK

CROSS-REFERENCE TO RELATED APPLICATIONS

The present application is a continuation of U.S. patent application Ser. No. 11/292,784, filed on Dec. 2, 2005, now U.S. Pat. No. 7,762,258, entitled "Infant Nasal Interface Mask", the contents of which are incorporated herein by reference and for all purposes.

BACKGROUND

The present invention relates to nasal masks for use with continuous positive airway pressure (CPAP) systems. More particularly, it relates to a mask worn over the nose of a patient, such as an infant, when receiving nasal CPAP therapy.

Continuous positive airway pressure (CPAP) therapy has been employed for many years to treat patients experiencing respiratory difficulties and/or insufficiencies. More recently, CPAP therapy has been advanced as being useful in assisting patients with under-developed lungs (in particular, infants and especially premature infants or neonates), by preventing lung collapse during exhalation and assisting lung expansion during inhalation.

In general terms, CPAP therapy entails the continuous transmission of positive pressure into the lungs of a spontaneously breathing patient throughout the respiratory cycle. A CPAP system generally includes a CPAP generator adapted to create or generate a continuous positive airway pressure within one or two tubes, along with a patient interface device connected to the generator that serves as a conduit for transfer of inhaled and exhaled gases. The CPAP system can assume a variety of forms, including a fixed flow, ventilator-type system, or a variable flow system.

CPAP can be delivered to the patient using a variety of patient interface devices, for example an endotracheal tube. With infants, however, it is more desirable to employ a less invasive patient interface device, in particular one that interfaces directly or indirectly with the nasal airways via the patient's nares. Such systems are commonly referred to as nasal continuous positive airway pressure (nCPAP) systems.

With nCPAP systems, the patient interface piece is typically either a dual prong body or a mask. The dual prong device includes two prongs or cannulas each sized for insertion within a respective nare of the patient. While a relatively stable fluid seal can readily be accomplished between the prongs and the nasal airways, some patients, especially infants, negatively react to the discomfort attendant with insertion of the prongs. Conversely, the nasal mask device is placed over the patient's nose and thus, in theory, will cause less patient discomfort. Unfortunately, currently available infant nCPAP masks have several shortcomings.

For example, available nCPAP masks are only somewhat flexible (especially relative to a point of interface with the CPAP system) and thus cannot accommodate any misalignment of the nCPAP generator relative to the patient's nose. When the nCPAP generator is later moved relative to the patient to correct this misalignment, the nCPAP mask will also move in a similar fashion, potentially leading to air leaks relative to the patient's face or general patient discomfort. This can be especially problematic with infants whom otherwise have small facial features and thus less available surface area for achieving and maintaining a fluid tight seal with the mask.

Along these same lines, it is oftentimes necessary to apply a fairly significant force to the nasal mask to ensure a fluid tight seal against the patient's nose/face. For example, a strap is commonly wrapped about the patient's head and connected to the CPAP generator. The CPAP generator, in turn, is assembled to the nasal mask such that a force placed on the CPAP generator by the strap is transferred onto the nasal mask in sealing the mask about the patient's nose. Because the conventional nasal mask may not readily conform to the contours of the patient's facial anatomy, the strap must be pulled tight so as to maintain the desired, fluid-tight seal. For certain patients, especially infants, this securing force can cause great discomfort, cause bruising and lead to skin necrosis. Also, the forces may be concentrated by the mask at a few pressure points on the patient's nose/face, further increasing the likelihood of long-term complications (e.g., sores or wounds on the patient's nasal septum, upper lip, nasal bridge, cheeks, etc.). Along these same lines, perhaps in an effort to promote complete contact with the patient's face, conventional nasal mask designs intimately contact the patient's upper lip directly at and below the nasal septum exterior. For many infants, the skin of the upper lip philtrum is delicate and highly sensitive, and can more easily succumb to necrosis when contacted by the mask. Regardless, an infant patient will react quite negatively to even minor discomfort associated with application of the nasal mask to his or her nose/face.

In light of the above, a need exists for an improved nasal mask for use with an nCPAP system, especially for infant patient applications.

SUMMARY

Some aspects in accordance with principles of the present invention relate to an infant nasal interface mask for use with a nasal continuous positive airway pressure (nCPAP) system. The mask includes a mask body and a base. The mask body forms a cavity and is defined by a leading portion, an intermediate shell portion, and a trailing portion. In this regard, the leading portion terminates in a leading edge forming an aperture open to the cavity and having a generally triangular shape for placement over a patient's nose. Further, the trailing portion includes a bellows segment characterized by an increased flexibility as compared to a flexibility of the intermediate shell portion. The base extends from the trailing portion opposite the leading portion and forms at least one longitudinal passage extending through a thickness of the base and fluidly connected to the cavity. With this in mind, the intermediate shell portion is laterally pivotable relative to the base via the bellows segment. In one embodiment, the trailing portion forms the bellows segment to have a reduced wall thickness as compared to a wall thickness of the intermediate shell portion. In other embodiments, the leading portion forms a patient contact face defining one or more contours providing for septum and/or ocular relief.

Other aspects in accordance with principles of the present invention relate to an infant nasal continuous positive airway pressure (nCPAP) device for use in an nCPAP system. The device includes an nCPAP generator and an infant nasal mask. The nCPAP generator includes first and second tubes fluidly connected to a fluid supply port, with the generator adapted to generate a continuous positive airway pressure within each of the tubes. The infant nasal mask is mounted to the tubes and includes a mask body and a base. The mask body forms a cavity and is defined by a leading portion, an intermediate shell portion, and a trailing portion. The leading portion terminates in a leading edge forming an aperture otherwise open to the cavity and having a generally triangular shape for placement over a patient's nose. The trailing portion includes a bellows segment characterized by an increased flexibility as compared to a flexibility of the intermediate shell portion. The base extends from the trailing portion opposite the leading portion and forms first and second passages extending longitudinally through a thickness of the base and fluidly connected to the cavity. In this regard, the passages are sized for assembly over a respective one of the tubes. In one embodiment, upon final assembly, the device is configured such that the intermediate shell portion is laterally pivotable relative to both the base and the tubes in a multiplicity of directions. In another embodiment, the nCPAP generator further includes a housing laterally surrounding the tube and sized to receive the base. Further, the base and the housing define corresponding, non-symmetrical perimeter shapes such that the base can only be assembled within the housing in a single orientation.

Yet other aspects in accordance with principles of the present invention relate to an infant nasal interface mask for use with an nCPAP system. The mask includes a mask body and a base. The mask body forms a cavity defined by a leading portion, an intermediate shell portion, and a trailing portion. The leading portion forms a patient contact face terminating in a leading edge otherwise forming an aperture open to the cavity. The aperture has a generally triangular shape for placement over a patient's nose. Further, the patient contact face has a reduced wall thickness as compared to a nominal wall thickness of the intermediate shell portion and defines opposing ocular reliefs and a septal relief feature. The trailing portion forms a bellows segment characterized by a reduced wall thickness as compared to a nominal wall thickness of the intermediate shell portion, along with a lateral bend in longitudinal extension. The base extends from the trailing portion opposite the leading portion and forms at least one longitudinal passage extending through a thickness of the base and fluidly connected to the cavity. With this in mind, the intermediate shell portion is laterally pivotable relative to the base via the bellows segment.

BRIEF DESCRIPTION OF THE DRAWINGS

FIG. 2 is a longitudinal cross-sectional view of the mask of FIG. 1A;

FIG. 3 is a front view of the mask of FIG. 1A;

FIG. 4 is a bottom view of the mask of FIG. 1A;

FIG. 5 is a rear view of the mask of FIG. 1A;

FIG. 6 is a transverse cross-sectional view of the mask of FIG. 1A;

DETAILED DESCRIPTION

Figure 1B:
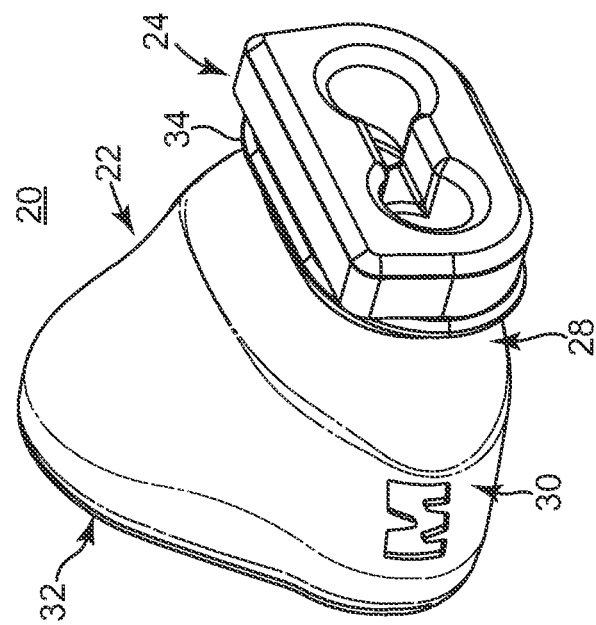
FIG. 1B is a rear perspective view of the mask of FIG. 1A.
Figure 1A:
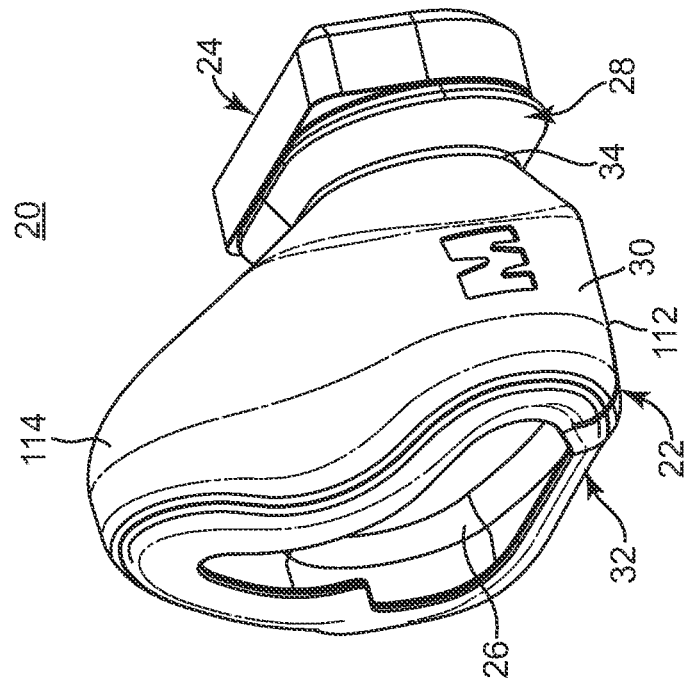
FIG. 1A is a front perspective view of an infant nasal interface mask in accordance with principles of the present invention.

One embodiment of an infant nasal interface mask 20 for use with a nasal continuous positive airway pressure (nCPAP) system is shown in FIGS. 1A and 1B. The mask 20 includes a mask body 22 and a base 24. The mask body 22 forms an internal cavity 26 (best shown in FIG. 1A), and is generally defined by a trailing portion 28, an intermediate shell portion 30, and a leading portion 32. Details on the various components are provided below. In general terms, however, the base 24 extends from the trailing portion 28 and is configured to establish a fluid connection between an nCPAP generator (shown at 150 in FIG. 7A) and the cavity 26. The trailing portion 28 forms a bellows segment 34 (referenced generally) adapted to permit and facilitate lateral pivoting and swiveling of the intermediate shell portion 30 relative to the base 24, as well as a cushioning effect whereby the bellows segment 34 can longitudinally compress. The leading portion 32, in turn, is configured for placement about and over a patient's nose (not shown). With this configuration, the mask 20 readily accommodates any slight misalignments upon securement to the patient, whereby the shell portion 30/leading portion 32 effectively "float" relative to the base 24. As described below, in some embodiments, the mask 20 incorporates additional features that further reduce possible patient discomfort. As used throughout the specification, directional terminology such as "proximal" and "distal" are used with reference to a position of the mask 20 relative to a patient to whom the mask 20 is applied. Thus, "proximal" is closer to the patient as compared to "distal".

The mask 20 is preferably an integral, homogenous structure, formed of a surgically safe, compliant material capable of achieving a fluid seal when applied to a patient's skin. For example, in one embodiment, the mask 20 is a molded silicone part. Alternatively, other materials such as soft vinyls, thermoplastic elastomers, etc., are also acceptable. In alternative embodiments, the mask 20 can have other forms, such as a gel-filled or air-filled bladder configuration. However, reference to certain dimensional attributes in the following discussion relates to one embodiment in which the mask 20, and in particular, the mask body 22, is a homogenous, thin-walled structure formed of silicon or silicone-like material.

In one embodiment, the mask body 22 includes a side wall that forms the portions 28-32 as a continuous structure that collectively define the internal cavity 26. With this in mind, FIG. 2 depicts a side wall 40 defining the trailing portion 28 as including a first section 42 and a second section 44 in longitudinal, proximal extension from the base 24, with the sections 42, 44 combining to form the bellows segment 34. As a point of reference, the base 24 generally defines a central axis C (FIG. 2) in longitudinal extension from the mask body 22. With this convention in mind, the first section 42 tapers inwardly relative to the central axis C in longitudinal (proximal) extension from the base 24, defining a first bend 46. In other words, a transverse cross-sectional area of the cavity 26 (i.e., perpendicular to the view of FIG. 2) decreases with longitudinal (proximal) extension of the first section 42 from the base 24. Conversely, the second section 44 projects laterally outwardly relative to the central axis C in longitudinal (proximal) extension from the first section 42, with the first and second sections 42, 44 combining to define a second bend 48. That is to say, the transverse cross-sectional area of the cavity 26 increases along the second section 44 in longitudinal (proximal) extension from the first section 42 to the intermediate shell portion 30. The first bend 46 defines a first bend angle .alpha., whereas the second bend 48 defines a second bend angle .beta.. The bend angles .alpha., .beta. can vary about a circumference of the mask body 22; in general terms, however, in a natural (or undeflected) state, the first bend angle .alpha. is less than 90 .degree. and the second bend angle .beta. is greater than 180 .degree. With this construction, the intermediate shell portion 30 can readily pivot and swivel relative to the base 24 via the bellows segment 34. For example, the intermediate shell portion 30 can pivot relative to the base 24 by compression of the bellows segment 34 along one side thereof and expansion of the bellows segment 34 at an opposite side. Further, the intermediate shell portion 30 can move longitudinally (distally) toward the base 24 (i.e., rightward relative to the view of FIG. 2) via compression of the bellows segment 34 primarily at or along the second bend 48 (compression may also occur at or along the first bend 46 in some embodiments). While the bellows segment 34 has been shown as including two of the bends 46, 48, in other embodiments, only one bend is formed (e.g., the first bend 46 can be eliminated); conversely, three or more bends can be provided in alternative embodiments.

To further enhance the flexibility afforded by the bellows segment 34, in one embodiment, at least a portion of the trailing portion 28 is characterized by a reduced thickness of the side wall 40 as compared to a thickness of the side wall 40 along the intermediate shell portion 30. For example and as shown in FIG. 2, in one embodiment an entirety of the first section 42 is characterized by a relatively uniform side wall 40 thickness, whereas the side wall 40 along the second section 44 has an increasing cross-sectional thickness in longitudinal, proximal extension from the first section 42 to the intermediate shell portion 30. Regardless, in one embodiment, at least a portion of the bellows segment 34, for example the first section 42, has a wall thickness that is at least 25% less than a maximum wall thickness of the intermediate shell portion 30. Alternatively, other dimensions and/or thickness relationships are acceptable. Regardless, by forming at least a portion of the trailing portion 28 to have a reduced wall thickness, an overall flexibility of the bellows segment 34 is enhanced, yet the intermediate shell portion 30 is provided with sufficient structural strength and rigidity to maintain the mask body 22 (and thus a majority of the cavity 26) in a desired shape during the delivery of CPAP therapy.

One or both of the bends 46, 48 and/or the reduced wall thickness described above renders the bellows segment 34 to have an increased lateral and longitudinal flexibility as compared to lateral and longitudinal flexibility of the intermediate shell portion 30. In further embodiments, one or both of the features allows the intermediate shell portion 30 to be laterally pivotable relative to the base 24 (and vice-versa) in a multiplicity of directions. To this end, in other alternative embodiments, the mask 20 can incorporate additional structural features/components that further enhance lateral pivoting and/or longitudinal flexibility of the intermediate shell portion 30 relative to the base 24 (and vice-versa).

As shown in FIGS. 1A and 1B, the intermediate shell portion 30 generally expands in outer dimension in proximal, longitudinal extension from the trailing portion 28 to the leading portion 32. Relative to a front planar view (FIG. 3) of the mask 20, the intermediate shell portion 30 generates a generally triangular-like exterior shape that in turn is reflected by a shape of the internal cavity 26. This triangular-like shape corresponds with human nasal anatomy, with the intermediate shell portion 30 defining a maximum height and width of the mask body 22 at or adjacent the leading portion 32. To this end, an overall size of the intermediate shell portion 30, and thus the internal cavity 26, is conducive for use with infant patients, yet is relatively small (and thus less obtrusive to an infant patient). For example, in one embodiment, the intermediate shell portion 30 defines a maximum height in the range of 0.5-1.25 inches and a maximum width in the range of 0.8-1.4 inches, although other dimensions are also acceptable. Notably, to better promote desired positioning of the nCPAP generator (not shown) relative to a patient during use, in one embodiment the intermediate shell portion 30 is not laterally centered relative the central axis C (FIG. 2) defined by the base 24. This off-set relationship is reflected in FIG. 2.

Alternatively, however, the intermediate shell portion 30 and the base 24 can be more closely aligned. Finally, the intermediate shell portion 30 has various contours along the exterior surface thereof, several of which are continued by the leading portion 32 as described below.

With specific references to FIGS. 2 and 3, the leading portion 32 extends from the intermediate shell portion 30 (FIG. 2) and generally includes a distal segment 60 and a proximal segment 62 (the segments 60, 62 being referenced generally in FIG. 3). The distal segment 60 extends in a generally longitudinal (proximal) fashion from the intermediate shell portion 30, whereas the proximal segment 62 extends from the distal segment 60 in a generally lateral fashion (i.e., inwardly relative to the central axis C), and terminates at a leading edge 64. The leading edge 64 defines an aperture 66 that is otherwise open to the cavity 26. To this end, the proximal segment 62 defines a patient contact face 68 (referenced generally) that otherwise contacts the patient (not shown) during use, with the patient's nose (not shown) extending through the aperture 66 and into the cavity 26.

With the above conventions in mind, in one embodiment at least the proximal segment 62, and preferably both the distal segment 60 and the proximal segment 62, are characterized by a decreased wall thickness as compared to that of the intermediate shell portion 30. This relationship is best shown in FIG. 2. The side wall 40 decreases in nominal thickness from the intermediate shell portion 30 to the distal segment 60, with this decreased thickness being maintained along an entirety of the proximal segment 62. By way of example, in one embodiment, a nominal wall thickness of the proximal segment 62 is at least 25% less than a maximum wall thickness of the intermediate shell portion 30. At least a portion of the distal segment 60 immediately adjacent the proximal segment 62 is similarly configured in terms of wall thickness. Further, a transition of the distal segment 60 to the proximal segment 62 is rounded or arcuate in transverse cross-section, thus reducing patient discomfort when in contact with the patient's face as well as promoting compliant, inward (distal) orientation of the proximal segment 62 relative to the distal segment 60. One or both of these preferred features render the proximal segment 62 highly flexible and compliant (as compared to the intermediate shell portion 30), thus allowing the patient contact face 68 to more readily conform to the various contours presented by the patient's facial anatomy when the patient contact face 68 is pressed against the patient (not shown). This, in turn, improves patient comfort and reduces possible pressure points on the patient's face that might otherwise lead to future complications. In alternative embodiments, the leading portion 32 need not have a differing wall thickness as compared to the intermediate shell portion 30.

In addition to, in one embodiment, being flexible and compliant, the leading portion 32, and in particular the proximal segment 62, is preferably sized and shaped to more closely match expected anatomical characteristics of the patient's face (not shown). For example, with specific reference to FIG. 3, relative to a frontal planar view of the mask body 22, the proximal segment 62, and in particular the patient contact face 68, generally defines or forms a lip region 80, first and second side regions 82, 84, and a bridge region 86. The side regions 82, 84 extend from opposite ends, respectively, of the lip region 80. Further, the side regions 82, 84 connect at the bridge region 86, that is otherwise formed opposite the lip region 80. The regions 80-86 combine to define a triangular-like shape. To this end, a perimeter 88 of each of the side regions 82, 84 forms an ocular relief feature or contour 90 (referenced generally). More particularly, the perimeter 88 of each of the side regions 82, 84 defines the ocular relief feature 90 as a concave curvature in extension from the lip region 80 to the bridge region 86 relative to a frontal plane or view of the mask body 22. The ocular relief feature 90 reduces or even eliminates the potential of pushing the patient's skin into or toward the patient's eye as the mask 20 is pressed against the patient's face, thus enhancing patient comfort.

To better ensure the elimination of air leaks around the patient's eyes, in one embodiment, the side regions 82, 84 have a fairly large width (i.e., lateral distance from the perimeter 88 to the leading edge 64) and further include or define a longitudinal (proximal) projection or contour that better matches the anatomical shape of the patient's face in a region between the nose and the eye. This relationship is best shown in the longitudinal cross-sectional view of FIG. 2 in which the side region 82 is illustrated as having a convex curvature feature 92 (i.e., longitudinally outward or proximal extension or projection relative to the intermediate shell portion 30) adjacent the bridge region 86. Alternatively, especially where the mask 20 is configured for use with very small infants, the convex curvature feature 92 can be reduced or eliminated.

Returning to FIG. 3, the lip region 80 is, in some embodiments, contoured to better match expected anatomical features of the patient, and in particular the patient's lip (e.g., region of the upper lip between the vermilion border and the nose, including the philtrum). For example, in one embodiment, the lip region 80 has a distal or inward curvature (best shown in FIG. 1A and also in FIG. 4) to anatomically match a protrusion of the patient's philtrum. In addition, in one embodiment, the lip region 80 defines a septal relief feature 100. The septal relief feature 100 is best shown in FIG. 3 and is characterized by the lip region 80 defining a convex lateral curvature in extension between the side regions 82, 84. That is to say, the lip region 80 projects or curves laterally outwardly or downwardly (relative to the upright orientation of FIG. 3) in extension between the side regions 82, 84. The septal relief feature 100 minimizes overt contact (and preferably eliminates any contact) between the lip region 80 and the patient's upper lip in the region adjacent the nasal septum (e.g., the philtrum skin) during use, thus minimizing opportunities for skin breakdown in this delicate area and increasing patient comfort.

In one embodiment, the mask body 22 includes all of the features 90, 92 and 100 described above. In alternative embodiments, one or more of the contour features 90, 92 and/or 100 can be altered or eliminated.

An additional feature of the mask body 22 in accordance with some embodiments of the present invention is further illustrated in FIG. 4. More particularly, in one embodiment, the intermediate shell portion 30 defines or forms a viewing window 110 (illustrated schematically) along a bottom face 112 thereof. As a point of reference, an overall, generally triangular shape of the mask body 22 dictates a desired orientation when applied over a patient's nose (not shown). More particularly, and with additional reference to FIG. 1A, the mask body 22 is sized and shaped to be secured over the patient's nose in the upright orientation shown. In conjunction with this upright orientation, then, the intermediate shell portion 30 thus defines a top face 114 and the bottom face 112. When applied over a patient's nose, the top face 114 is proximate a bridge of the patient's nose, whereas the bottom face 112 is proximate (below) the patient's nasal septum/philtrum. With these conventions in mind, and returning to FIG. 4, the viewing window 110 facilitates viewing of the patient's nares and/or nasal septum once the mask body 22 is applied over the patient's nose. The viewing window 110 can assume a variety of forms, but does not negatively affect an ability of the mask body 22 to establish a fluid-tight seal over the patient's facial anatomy/nasal airways. Further, the viewing window 110 preferably does not negatively affect an overall structural rigidity of the intermediate shell portion 30. With these constraints in mind, in one embodiment, the viewing window 110 is formed and characterized as exhibiting an opacity that is less than an opacity of a remainder of the intermediate shell portion 30. For example, in one embodiment, the mask body 22, preferably an entirety of the mask 20, is integrally and homogeneously formed as a continuous, molded part comprising a silicone plastic. With this in mind, the mold from which the mask body 22 is formed can be highly polished in the region corresponding to the viewing window 110, thus decreasing an opacity of the intermediate shell portion 30 at the viewing window 110 as compared to a remainder of the intermediate shell portion 30. Alternatively, the viewing window 110 can be formed in a variety of other ways, and can be formed at one or more locations in addition to, or instead of, the bottom face 112. Even further, in other embodiments, the viewing window 110 is eliminated.

With reference to FIGS. 5 and 6, the base 24 extends from the trailing portion 28 and in one embodiment forms first and second passages 120, 122, and a channel 124. The passages 120, 122 extend in a longitudinal fashion (e.g., parallel with the base central axis C) through a thickness of the base 24, and are fluidly connected to the cavity 26 as shown best in FIG. 6. As described in greater detail below, the passages 120, 122 are sized for assembly over corresponding components of a CPAP generator device (shown at 150 in FIG. 7A), and thus are open relative to a rear face 126 of the base 24. Thus, the passages 120, 122 provide a mechanism for fluidly connecting the CPAP generator device to the cavity 26. The channel 124 extends between, and is fluidly connected to, the passages 120, 122. In addition, while the channel 124 is open at the rear face 126, the channel 124 is not directly fluidly connected to the cavity 26. As described in greater detail below, the channel 124 is sized and shaped in accordance with certain features of one embodiment CPAP generator device, and facilitates sampling or tapping of pressure within the device. Thus, the channel 124 can assume a wide variety of forms. In fact, in some embodiments, the channel 124 is eliminated. Similarly, while two of the passages 120, 122 are shown, in other embodiments, the base 24 can form only one, or more than two, of the passages 120, 122.

With specific reference to FIG. 5, the base 24 is, in one embodiment, sized and shaped for interfacing with a corresponding component of a CPAP generator device (shown at 150 in FIG. 7A) and fluidly connecting the passage(s) 120 and/or 122 to the CPAP generator device. In this regard, an exterior of the base 24 defines a perimeter 130 (best shown in FIG. 5) that includes opposing first and second side edges 132, 134 and opposing, first and second end edges 136, 138. In one embodiment, an intersection or transition of the first side edge 132 to each of the end edges 136, 138 differs from the transition or intersection of the second side edge 134 to the end edges 136, 138. For example, in one embodiment, transition of the second side edge 134 to each of the end edges 136, 138 is characterized as being arcuate or curved, having a relatively large radius of curvature. In contrast, a transition of the first side edge 132 to each of the end edges 136, 138 is characterized as defining a relatively distinct corner, having a radius curvature that is less than that of the second side edge 134/end edge 136, 138 transitions. Thus, a lateral length of the first side edge 132 is greater than that of the second side edge 134. This one preferred configuration of the perimeter 130 corresponds with feature(s) of the CPAP generator device so as to ensure a desired, proper orientation of the base 24, and thus the mask body 22, relative to the CPAP generator device upon final assembly.

Figure 7A:
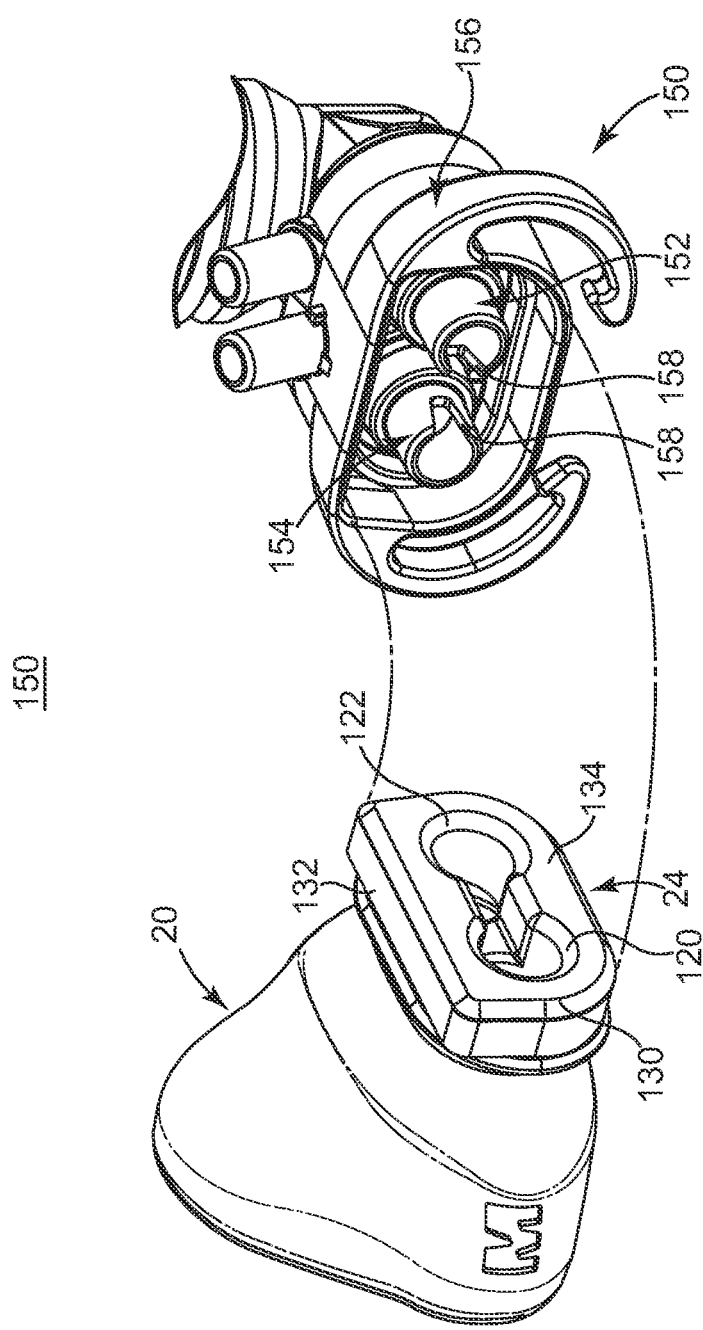
FIG. 7A is an exploded, perspective view of an nCPAP device in accordance with principles of the present invention including the mask of FIG. 1A and an nCPAP generator.

For example, FIG. 7A illustrates a portion of one embodiment CPAP generator device 150 with which the mask 20 is useful in accordance with principles of the present invention. Details on embodiments of the CPAP device 150 are provided in U.S. Pat. No. 7,578,294 entitled "Nasal Continuous Positive Airway Pressure Device and System," issued on Aug. 25, 2009, the teachings of which are incorporated herein by reference. In general terms, the CPAP device 150 includes first and second tubes 152, 154 laterally surrounded by a housing 156. During use, the CPAP device 150 generates a continuous positive airway pressure within each of the tubes 152, 154. With these general concepts in mind, the passages 120, 122 of the base 24 are sized for mating over a respective one of the tubes 152, 154, and the base 24 received and frictionally retained within the housing 156. In this regard, an internal perimeter shape of the housing 156 corresponds with the perimeter 130 of the base 24 as previously described.

In particular, the differing lengths of the side edges 132, 134, as well as the curved and corner-shaped transition regions previously described prevents a user from accidentally attempting to insert the base 24 into the housing 156 in an orientation opposite to that desired (i.e., the upright orientation). That is to say, the base 24/housing 156 interface permits only one orientation of the base 24, and thus of the mask 20, relative to the CPAP device 150.

Figure 7B:
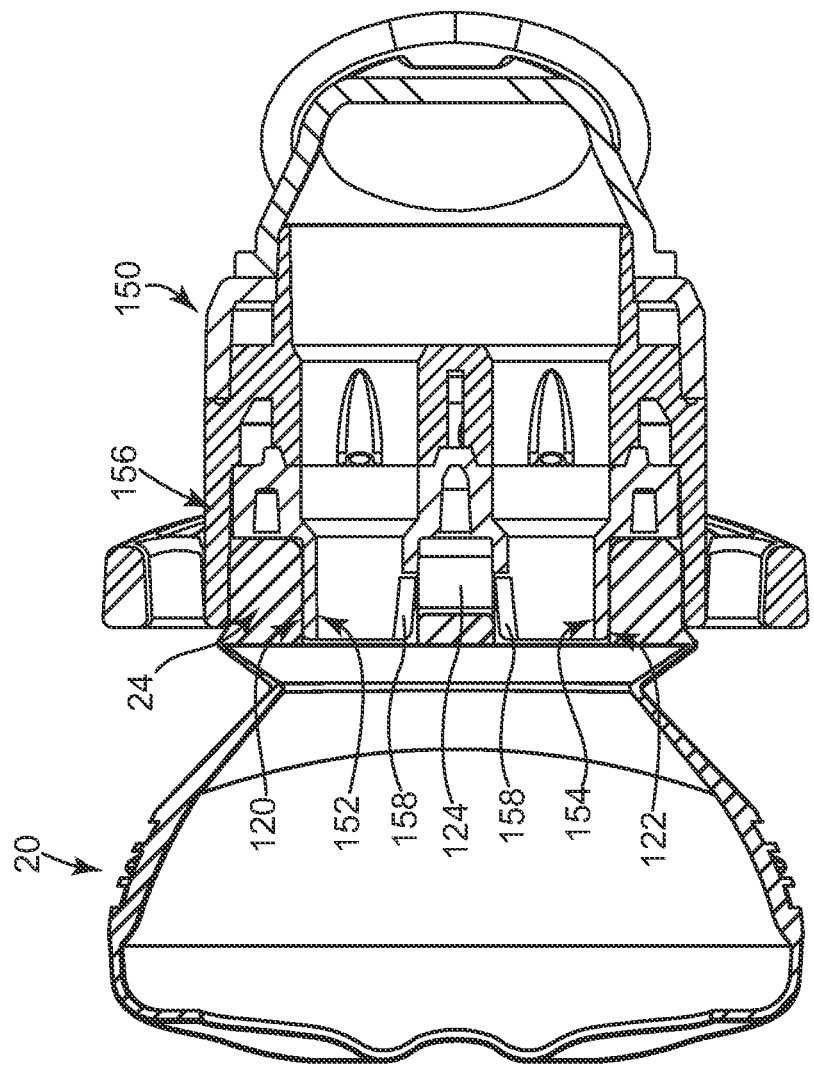
FIG. 7B is a cross-sectional view of the nCPAP device of FIG. 7A upon final assembly.

FIG. 7B partially illustrates assembly of the base 24 to the CPAP device 150, and in particular, the first passage 120 over the first tube 152 and the second passage 122 over the second tube 154. As shown, each of the tubes 152, 154 includes a radial slot 158 that is otherwise fluidly connected to the channel 124 upon final assembly of the base 24 within the housing 156. With this one arrangement, then, airflow within the tube 154 is allowed to flow from the tube 154/base 24 interface, via the channel 124, for subsequent pressure monitoring. In one embodiment a depth and width of the channel 124 is correlated with a diameter of the passages 120, 122 to minimize formation of back pressure within the device 20 during delivery of CPAP therapy while still affording the ability to accurately sample pressure being delivered to the patient. To this end, it has surprisingly been found that by forming the channel 124 to have a depth that is at least 30% of the diameter of either passage 120, 122 and a width that is at lest 25% of either passage 120, 122 diameter, significant back pressure will not be generated at expected CPAP levels.

Although the mask 20 has been described in connection with certain features of the CPAP device 150, a wide variety of differing CPAP device configurations can also be employed. That is to say, the mask 20 in accordance with principles of the present invention is not limited to any one particular CPAP device design.

Figure 8:
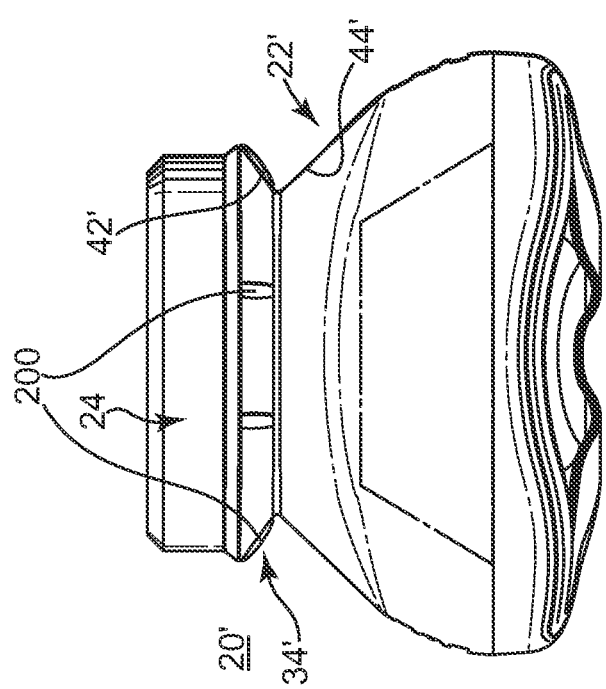
FIG. 8 is a side longitudinal cross-section view of an alternative embodiment infant nasal interface mask in accordance with principles of the present invention.

The infant nasal interface mask in accordance with principles of the present invention provides a marked improvement over previous designs. The thin-walled, bellows segment allows the shell/patient face of the mask to easily pivot and/or flex relative to the base (and thus the CPAP generator to which the base is assembled). This attribute allows the mask to accommodate any misalignments of the CPAP generator and/or related fixation device relative to the patient, and further minimizes or eliminates pressure point(s) on the infant's/patient's nose or face that might otherwise be created by CPAP generator misalignment. Other mask features in accordance with alternative embodiments further promote patient comfort and assembly to, and operation of, the CPAP generator. For example, an alternative embodiment infant nasal interface mask 20' is shown in FIG. 8, and is similar in many respects to the mask 20 (FIG. 1A) previously described. Thus, the mask 20' includes a mask body 22' and a base 24, with the mask body 22' forming a bellows segment 34'. The bellows segment 34' is similar to previous embodiments, and includes first and second wall sections 42', 44', as well as one or more ribs 200. The rib(s) 200 project laterally outwardly along one or both of the wall sections 42', 44', and provide a tactile indication to a user/physician that the bellows segment 34' has been overtly compressed or collapsed, a condition that might otherwise lead to airflow exchange complications. For example, the ribs 200 resist further contraction of the bellows segment 34' as the second section 44' contacts the ribs 200, and can even "force" the bellows segment 34' to revert back toward an uncompressed state.

Although the present disclosure has been described with reference to preferred embodiments, workers skilled in the art will recognize that changes can be made in form and detail without departing from the spirit and scope of the present disclosure.

What is claimed is:

1. An nasal interface mask for use with a nasal continuous positive airway pressure (nCPAP) system, the nasal interface mask comprising:
   a mask body forming a cavity and defined by a leading portion, an intermediate shell portion, and a trailing portion, wherein:
      the leading portion terminates in a leading edge forming an aperture open to the cavity and having a generally triangular shape for placement over a patient's nose, and
      the trailing portion includes a bellows segment disposed within the cavity and characterized by an increased flexibility as compared to a flexibility of the intermediate shell portion; and
   a base extending from the trailing portion opposite the leading portion, the base forming at least one passage extending longitudinally through a thickness of the base from an opening in a rear face of the base and permanently fluidly open to the aperture, wherein an axis of the opening intersects the aperture;
   wherein the intermediate shell portion is longitudinally moveable and laterally pivotable relative to the base via the bellows segment,
   wherein the mask body includes a side wall forming at least the intermediate shell and trailing portions, and
   wherein the bellows segment is characterized by the side wall having a reduced cross-sectional thickness along the bellows segment as compared to a nominal thickness of the side wall along at least a segment of the intermediate shell portion.

2. The nasal interface mask of claim 1, wherein the bellows segment is further characterized by the side wall forming a first bend in longitudinal extension from the base.

3. The nasal interface mask of claim 2, wherein the bellows segment includes the side wall defining a first section extending generally longitudinally from the base and a second section extending generally longitudinally from the first section toward the intermediate shell portion, and further wherein the first section forms the cavity to have a proximally decreasing transverse cross-sectional area to define the first bend relative to the base, and the second section forms the cavity to have a proximally increasing transverse cross-sectional area to define a second bend relative to the first section.

4. The nasal interface mask of claim 2, wherein the side wall forms a second bend along the bellows segment in longitudinal extension from the base.

5. The nasal interface mask of claim 1, wherein the leading portion includes a distal segment extending in a substantially longitudinal fashion from the intermediate shell portion, and a proximal segment extending in a substantially lateral fashion from the distal segment to the leading edge.

6. The nasal interface mask of claim 5, wherein a wall thickness of the mask body along the proximal segment is less than a wall thickness of the mask body along the intermediate shell portion.

7. The nasal interface mask of claim 5, wherein a transition from the distal segment to the proximal segment forms a curve in longitudinal cross-section.

8. The nasal interface mask of claim 1, wherein the leading portion forms a patient contact face in a plane generally perpendicular to a longitudinal axis defined by the base, the patient contact face including a lip region configured for placement at a patient's upper lip, and first and second side regions extending from opposite ends of the lip region and connecting at a bridge region formed opposite the lip region to define a substantially triangular shape, and further wherein a perimeter of the first and second side regions forms an ocular relief.

9. The nasal interface mask of claim 8, wherein the perimeter of the first and second side regions defines a first and a second concave curvatures in extension from the lip region to the bridge region relative to a frontal plane of the mask, the first and second concave curvatures comprising the ocular relief.

10. The nasal interface mask of claim 1, wherein the leading portion forms a patient contact face in a plane generally perpendicular to a longitudinal axis defined by the base, the patient contact face including a lip region configured for placement a patient's upper lip, and first and second side regions extending from opposite ends of the lip region and connecting at a bridge region formed opposite the lip region to define a substantially triangular shape, and further wherein the lip region defines a septal relief feature.

11. The nasal interface mask of claim 10, wherein the septal relief feature is characterized by the lip region forming a laterally outward, convex curvature.

12. The nasal interface mask of claim 1, wherein a first zone of the mask body has an opacity less than an opacity of a second zone to define a viewing window.

13. The nasal interface mask of claim 12, wherein the intermediate shell portion defines a bottom face and a top face, the nasal interface mask being configured to generate a desired orientation upon placement over a nose of a patient in which the bottom face is proximate an upper lip of the patient and the top face is adjacent a bridge of the patient's nose, and further wherein the first zone is defined in the bottom face to facilitate viewing a patient's septum and nares during use.

14. The nasal interface mask of claim 1, wherein a nominal thickness of the side wall along the bellows segment is at least 50% less than a nominal thickness of the side wall along the intermediate shell portion.

15. The nasal interface mask of claim 1, wherein a nominal thickness of the side wall along at least a segment of the leading portion is less than a nominal thickness of the side wall along at least a segment of the intermediate shell portion.

16. The nasal interface mask of claim 1, wherein the leading portion forms a patient contact face in a plane generally perpendicular to a longitudinal axis defined by the base, the patient contact face including a lip region configured for placement at a patient's upper lip, and first and second side regions extending from opposite ends of the lip region and connecting at a bridge region formed opposite the lip region to define a substantially triangular shape, and further wherein relative to a side plane of the mask, each of the side first and second regions forms a convex curvature feature.

17. The nasal interface mask of claim 1, wherein the base is configured to define, in transverse cross-section, opposed first and second side edges, and opposed first and second end edges, and further wherein a transition between the first end edge and the first side edge defines a radius of curvature greater than a radius of curvature defined at a transition between the first end edge and the second side edge.

18. The nasal interface mask of claim 1, wherein the at least one passage includes a pair of passages extending through a thickness thereof, and a channel extending between, and fluidly connected to, the pair of passages.

19. The nasal interface mask of claim 1, wherein apart from the opening in the rear face and a fluid connection to the cavity, the at least one passage is closed relative to an exterior of the base.

20. The nasal interface mask of claim 1, wherein the bellows segment includes a plurality of ribs projecting outwardly to resist contraction of the bellows segment.

21. A nasal continuous positive airway pressure (nCPAP) device for use in an nCPAP system, the device comprising:
 an nCPAP generator comprising:
  first and second tubes fluidly connected to a fluid supply port, the nCPAP generator adapted to generate a continuous positive airway pressure within each of the first and second tubes; and
 a nasal mask mounted to the first and second tubes, the mask comprising:
  a mask body forming a cavity and defined by a leading portion, an intermediate shell portion, and a trailing portion, wherein:
   the leading portion terminates in a leading edge forming an aperture open to the cavity and having a generally triangular shape for placement over a patient's nose,
   the trailing portion includes a bellows segment characterized by an increased flexibility as compared to a flexibility of the intermediate shell portion, and
   the bellows segment includes one or more ribs projecting laterally outwardly along a section of a side wall of the bellows segment in the mask body to resist contraction of the bellows segment and to apply a force to revert the bellows segment to an uncompressed state, and
  a base extending from the trailing portion opposite the leading portion, the base forming a pair of passages extending in a longitudinal fashion through a thickness of the base and fluidly connected to the cavity, respective ones of the pair of passages being sized for assembly over a respective one of the first and second tubes,
  wherein the nCPAP generator further comprises a housing laterally surrounding the first and second tubes, the housing sized to receive the base, and
  wherein the base and the housing define corresponding, nonsymmetrical perimeter shapes.

22. The nCPAP device of claim 21, wherein upon final assembly, the nCPAP device is configured such that the intermediate shell portion is laterally pivotably relative to the base and the first and second tubes in a multiplicity of directions.

* * * * *